United States Patent [19]

Iwasaki

[11] 4,118,975
[45] Oct. 10, 1978

[54] LOADING SHAFT POSITIONING APPARATUS FOR HARDNESS TESTER

[75] Inventor: Shozo Iwasaki, Ebina, Japan

[73] Assignee: Kabushiki Kaisha Akashi Seisakusho, Japan

[21] Appl. No.: 824,701

[22] Filed: Aug. 15, 1977

[30] Foreign Application Priority Data

Dec. 16, 1976 [JP] Japan .............................. 51/151159
Apr. 4, 1977 [JP] Japan .............................. 52/38266

[51] Int. Cl.² .............................................. G01N 3/44
[52] U.S. Cl. .............................................. 73/81; 73/83
[58] Field of Search .............................. 73/81, 83, 82

[56] References Cited

U.S. PATENT DOCUMENTS 2,357,856  9/1944  Tate ........................................ 73/82
2,554,206  5/1951  Pearson et al. ........................ 73/83

FOREIGN PATENT DOCUMENTS 1,069,365  5/1967  United Kingdom ........................ 73/83

Primary Examiner—Anthony V. Ciarlante
Attorney, Agent, or Firm—Robert E. Burns; Emmanuel L. Lobato; Bruce L. Adams

[57] ABSTRACT

An apparatus for positioning a loading shaft of hardness tester prior to application of test load. A loading shaft position detector is provided for detecting the arrival of the loading shaft at a given position when elevating it, and the detector controls an electromagnetic means to check further continuation of the elevating operation of the loading shaft so that the loading shaft is set automatically at the given position. An electromagnetic clutch or brake serves as the electromagnetic means.

4 Claims, 3 Drawing Figures

LOADING SHAFT POSITIONING APPARATUS FOR HARDNESS TESTER

BACKGROUND OF THE INVENTION

This invention relates to loading shaft positioning apparatus for hardness tester. More particularly, it relates to loading shaft positioning apparatus employing electomagnetic means.

Generally, in applying a test load on specimen on a hardness testing machine, it is a common practice to predetermine the position of its loading shaft so that the load is applied in the optimum condition.

Conventionally, this positioning of the hardness tester loading shaft has been effected by elevating a screw shaft fitted on the underside of the anvil. By this, the loading shaft adapted to contact for the specimen, while reading the resulting upward displacement of the loading shaft on an indicator. The loading shaft elevating work is performed manually so that the upward displacement (i.e., the reading on the indicator) falls within a given range.

However, such conventional positioning means requires incessant reading of the indicator while elevating the loading shaft, so that the elevation be stopped when the reading falls within the given range. Accordingly, considerable attentiveness and skill have been demanded.

SUMMARY OF THE INVENTION

This invention aims at solving such problem with the conventional loading shaft positioning means. The object of this invention is to provide a manually operable loading shaft positioning apparatus for hardness tester, which uses an electromagnetic system for stoppage of a loading shaft elevating operation when the loading shaft reaches the desired position, thus semi-automatically preventing further continuation of the elevating operation, and thereby setting the loading shaft in the desired position.

To achieve the above object, apparatus according to this invention can use a loading lever whose base is swingably pivoted to the hardness tester body, a loading shaft adapted to engage with said loading lever, a specimen supporting screw shaft vertically movably fitted to said body so as to push up said loading shaft through a specimen, a manually rotatable operating nut screwed onto said screw shaft to elevate it, a loading shaft position detector that detects the arrival at a given position of the loading shaft that is pre-elevated thereto before engaging with the descending loading lever, and electromagnetic means to fix said operating nut by the operation of the detector. An electromagnetic clutch or brake serves as said electromagnetic means.

Said electromagnetic brake comprises a movable magnetic member elevatably fitted below said nut so as to be integrally rotatable therewith and a fixed electromagnet attached to said body so as to attract and fix said movable magnetic member by receiving exciting current when said detector operates.

BRIEF DESCRIPTION OF THE DRAWINGS

Now preferred embodiments of this invention will be described by reference to accompanying drawings.

FIGS. 2 and 3 show a second embodiment of this invention, in which FIG. 2 is a front view showing, in partial and vertical section, the principal portion thereof and FIG. 3 is a plan view of a movable magnetic member in its electromagnetic brake.

DESCRIPTION OF THE PREFERRED EMBODIMENTS

Figure 1:
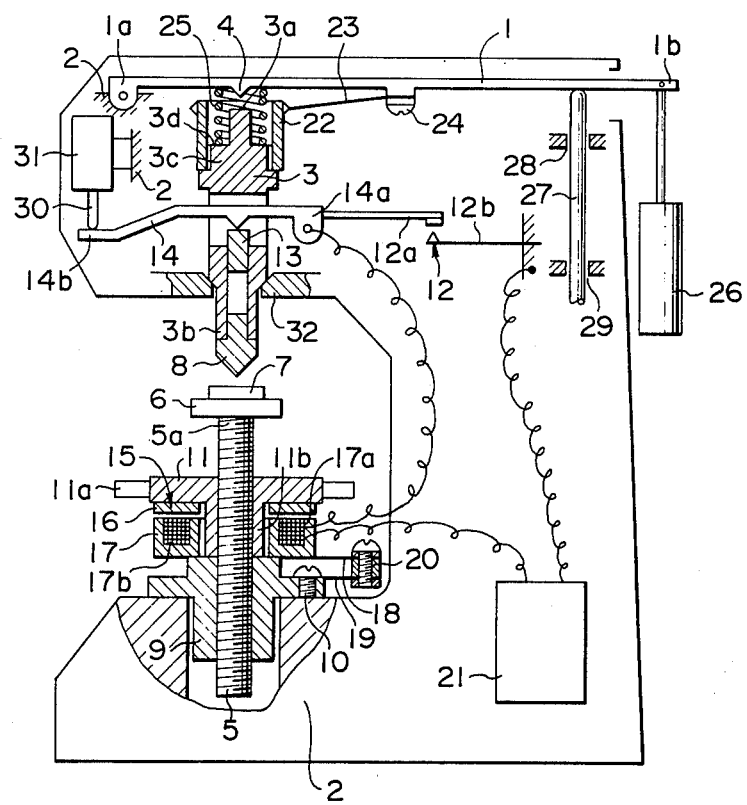
FIG. 1 is a front view showing, in partial and vertical section, the principal portion of a first embodiment of loading shaft positioning apparatus for hardness tester according to this invention.

The first embodiment of the invention will be described first. As illustrated in FIG. 1, the base end 1a of a loading lever 1 is swingably pivoted to a hardness tester frame or body 2.

A loading shaft 3 extends vertically, with its top end 3a adapted to engage with a knife edge 4 formed on the lower side of said loading lever 1 close to the base end 1a.

A specimen anvil 6 rests on the top end 5a of an externally threaded specimen supporting screw shaft 5. The screw shaft 5 is elevatably inserted in a guide cylinder 9 provided in the body 2 so as to push up the loading shaft 3, by a specimen 7 placed on the anvil 6 and an indenter 8 fitted to the bottom end 3b of the loading shaft 3.

The guide cylinder 9 is fixed to the body 2 with a screw 10. The screw shaft 5 is inserted in the guide cylinder 9 coaxially with the loading shaft 3. The guide cylinder 9 and screw shaft 5 have a rotation preventing key and a key groove not shown, respectively, whereby the screw shaft is nonrotatable in the guide cylinder, while it, as mentioned, is elevationable (longitudinally movable) therein.

An operating nut 11 having an externally protruding handle 11a is threadedly connected with the screw shaft 5, for the elevating of that shaft, and its subsequent, threadwise return.

A switch 12 serving as a loading shaft position detector to detect the arrival of the loading shaft at a given position is provided in order to control the elevation of the top end 3a of the loading shaft 3 thereto prior to engagement with the loading lever 1.

The switch 12 comprises a first contact 12a attached to the base end 14a of an amplifying lever 14 which amplifyingly transmits the elevation displacement of the loading shaft 3 through a mechanical connector 13 fitted thereto, and a second contact 12b attached to the body 2.

Instead of using first contact 12a and second contact 12b, the switch 12 serving as the loading shaft position detector may be a relay, a microswitch actuated by the displacement of the loading shaft 3 or amplifying lever 14, or an electronic circuit switch actuated by the electric output generated by electrically converting such displacement.

An electromagnetic clutch 15, serving as said electromagnetic means, is interposed between the operating nut 11 and guide cylinder 9 so as to fix the nut 11 on closure of the switch 12.

The electromagnetic clutch 15 comprises an armature or first annular magnetic member 16 fixed below the nut 11, and; in magnetic circuit therewith an annular and cylindrical second magnetic member 17 freely mounted on a lower cylindrical projection 11b formed on the nut 11 so as to oppose said first magnetic member 16 leaving a slight space therebetween. A coil 17b is incorporated in an annular groove 17a cut in the top surface of the second magnetic member 17.

The second magnetic member 17 is attached to the guide cylinder 9 with the screw 10 through plate springs 18 and 19 and a connecting piece 20. Consequently, the second magnetic member 17 is not permitted to rotate, but to move only axially with respect to the screw shaft 5 and the lower cylindrical projection 11b on the nut 11.

One end of the coil 17b connects with the first contact 12a and the other end thereof with the second contact 12b through a power supply 21.

The first and second magnetic members 16 and 17 are made of such materials as pure iron, silicon steel, permalloy and ferrite.

The upper part 3c of the loading shaft 3, having an upward projecting center piece with end 3a, is screwed for a spring receiving cylinder 22. One end of a plate spring 23 is fitted to the top of the spring receiving cylinder 22 to support this cylinder and thereby the loading shaft 3.

The opposite end of the plate spring 23 is fixed with a screw 24 to the under side of the loading lever 1.

The plate spring 23 is so disposed as to extend substantially horizontally parallel to lever 1 when the knife edge 4 comes in contact with the top end 3a of the loading shaft 3. In their illustrated, free position these parts 3a and 4 are spaced by a reference load applying coil spring 25.

The reference load applying coil spring 25 is interposed between the loading lever 1 and the top shoulder 3d surrounding the center piece of the loading shaft 3 so as to enclose the knife edge 4.

A test load applying weight 26 hangs from the free end 1b of the loading lever 1.

To control the test load applied by this weight 26, a control shaft 27 is provided so as to contact the lower side of the loading lever 1 close to the free end 1b. Also, a cam or other means (not shown) to move the control shaft 27 up and down through guide holes 28 and 29 made in the body 2 is provided so as to contact the bottom end of the control shaft 27.

The test load can also be applied electromagnetically by employing electromagnetic means in stead of the weight 26.

A displacement gauge 31 fitted to the body 2 rests on the free end 14b of the amplifying lever 14 through a spindle 30.

Reference numeral 32 in the figure designates a stopper and loading shaft support formed in the body 2 so as to engage with the lower portion of the loading shaft 3.

In the loading shaft positioning apparatus for hardness tester of this invention thus constructed, the top end 3a of the loading shaft 3 is pushed up to a given position before the loading lever 1 descends and engages therewith.

This positioning is effected, and the arrival at the given position is detected as follows:

The handle 11a of the operating nut 11 is manually operated to raise the screw shaft 5, whereby the specimen 7 on the anvil 6 also rises accompanyingly.

On further raising the screw shaft 5 by operating the handle 11a, the specimen 7 comes in contact with the indenter 8. As the screw shaft 5 elevates further, the loading shaft 3 ascends against the force of the reference load applying spring 25.

Thereby the amplifying lever 14 turns through the mechanical connector 13 about the base end 14a, and the fist contact 12a of the switch 12 turns in the opposite direction.

By further raising the screw shaft 5 by operating the handle 11a of the operating nut 11, the loading shaft 3 is raised to the given position, whereupon the first contact 12a of the switch 12 contacts the second contact 12b.

When the first and second contacts 12a and 12b thus come in contact, a closed circuit connects the switch 12, coil 17b of the electromagnetic clutch 15 and power supply 21. Consequently, electric current flows through the coil 17b and the second magnetic member 17 becomes magnetized. The second magnetic member 17 is therefore attracted to the first magnetic member 16, whereby the electromagnetic clutch 15 fixes the operating nut 11.

In other words, on the engagement of the electromagnetic clutch 15 following the current passage through the coil 17b and the attraction between the first and second magnetic members 16 and 17, the operation of the handle 11a can no longer be continued, since the first magnetic member 16 is fixed to the lower side of the operating nut 11 and the second magnetic member 17 is not permitted to rotate but to move only axially along the screw shaft 5 and the lower cylidrical projection 11b of the nut 11. Accordingly, the loading shaft 3 stops at the given position. At this moment, as the second magnetic member rises due to deflection of the plate springs 18 and 19 and engages with the first magnetic member 16, no magnetic vertical pulling force is applied to the nut 11.

Thus as the manually elevated loading shaft 3 reaches the given position, the switch 12 operates and the electromagnetic clutch 15 fixes the operating nut 11 to automatically discontinue the operation of the handle 11a to raise the loading shaft 3. Thereby the loading shaft 3 is semiautomatically raised to the given position simply, easily and accurately.

To measure the hardness of the specimen 7, the cam etc. not shown is then driven to lower the control shaft 27, whereupon the test load imposed by the weight 26 is transmitted through the loading lever 1, knife edge 4, loading shaft 3 and indenter 8 to the specimen 7. Consequently, the indenter 8 produces an indentation corresponding to the hardness of the specimen 7.

By measuring the indentation with the displacement gauge 31 or a microscope (not shown), the hardness of the specimen 7 can be determined.

Figure 2:
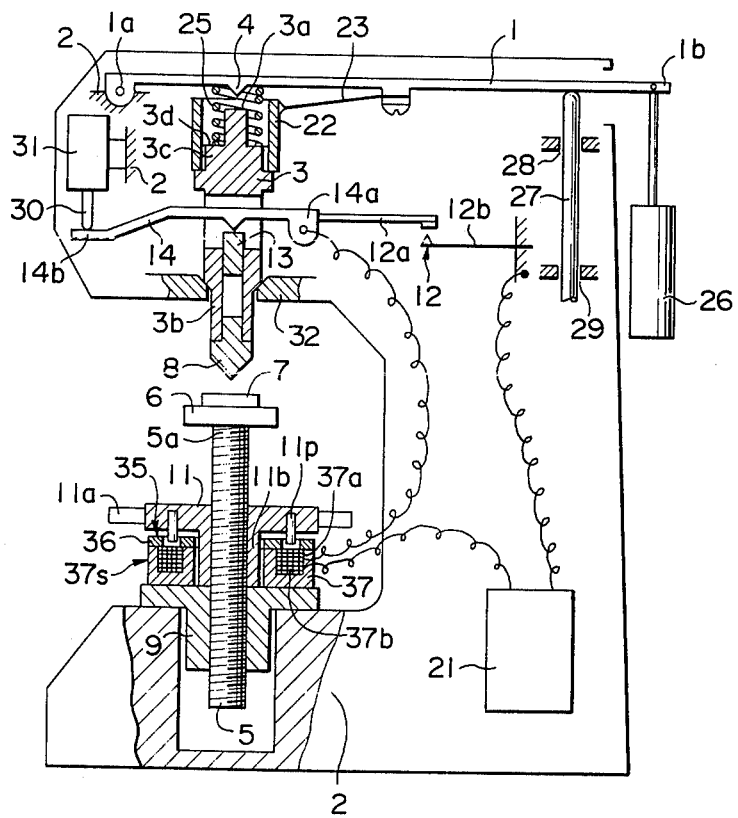

Next, the second embodiment of this invention will be described. In FIG. 2, similar reference numerals as used in FIG. 1 denotes similar parts. An electromagnetic brake 35 serving as the electromagnetic means is interposed between the nut 11 and guide cylinder 9 so as to fix the operating nut 11 by the operation of the switch 12.

The electromagnetic brake 35 comprises a movable magnetic member 36, fitted below the nut 11 and elevatably and integrally rotatably movable with the same, and a fixed magnet 37s attached through the guide cylinder 9 to the body 2 so as to attract and fix the movable magnetic member 36 on being magnetized as the switch 12 closes.

Figure 3:
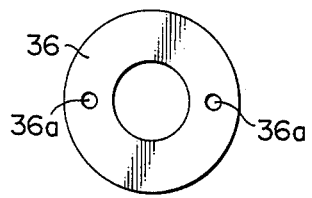

The movable magnetic member 36 is annularly shaped and has a pair of small holes 36a as shown in FIG. 3. A pair of pins 11p projecting from the under surface of the nut 11 engage with said small holes 36a, whereby the movable magnetic member 36 is permitted not only to elevate but also to rotate integrally with the nut 11.

The magnet 37s comprises a fixed annular and cylindrical magnetic member 37 concentrically disposed with the cylindrical projection 11b below the nut 11, and a coil 37b incorporated in an annular groove 37a in the upper surface of the fixed magnetic member 37. The magnetic member 37 is fixed on the upper surface of the guide cylinder 9.

One end of the coil 37b connects with the first contact 12a and the other end thereof with the second contact 12b through the power supply 21.

The movable and fixed magnetic members 36 and 37 are made of such materials as pure iron, silicon steel, permalloy and ferrite.

To push up the top end 3a of the loading shaft 3 of the second embodiment to a given position prior to engagement with the loading lever 1 and detect its arrival at the given position, the handle 11a of the operating nut 11 is operated as in the case of the previously described first embodiment. By thus elevating the screw shaft 5, the loading shaft 3 is pushed up to the given position, whereupon the first contact 12a of the switch 12 comes in contact with the second contact 12b.

As the first contact 12a contacts the second contact 12b, a closed circuit connecting the switch 12, coil 37b of the electromagnetic brake 35, and power supply 21 is formed. Then, electric current flows to the coil 37b, whereupon the fixed magnetic member 37 becomes magnetized and functions as the magnet 37s. The fixed magnetic member 37 attracts and engages with the movable magnetic member 36, whereby the electromagnetic brake 35 fixes the operating nut 11. At this moment, no vertical force is applied to the nut.

In other words, as electric current flows to the coil 37b and the movable magnetic member 36 engages with the fixed magnetic member 37 as a result of attraction, the operation of the handle 11a becomes discontinued, since the movable magnetic member 36 is so disposed as to rotate integrally with the operating nut 11 and the fixed magnetic member 37 is fixed to the body 2 through the guide cylinder 9. Consequently, the loading shaft 3 stops at the given position.

Thus, as the loading shaft 3 reaches the given position, the switch 12 operates and the electromagnetic brake 35 fixes the operating nut 11, thereby automatically discontinuing the operation of the handle 11a, i.e., the elevation of the loading shaft 3. Accordingly, the elevation of the loading shaft 3 to the given position can be achieved very simply, easily and accurately.

In this apparatus, the movable magnetic member 36 always rests on the fixed magnet 37s and does not move vertically. This eliminates shock that might otherwise occur when the fixed magnet 37s attracts and fixes the movable magnetic member 36.

Further, since the movable magnetic member 36 always contacts the fixed magnet 37s, it is possible to reduce the size of the fixed magnet 37s by making small the product of the number of turns of the coil 37b of the fixed magnet 37s and current or ampere-turn.

After the elevation of the screw shaft 5 has been thus stopped, the cam etc. not shown is driven to lower the control shaft 27. Then the test load applied by the weight 26 is transmitted through the loading lever 1, knife edge 4, loading shaft 3 and indenter 8 to the specimen 7, and the indenter 8 produces an indentation corresponding to the hardness of the specimen 7.

By measuring the indentation with the displacement gauge 31 or a microscope (not shown), the hardness of the specimen 7 can be determined.

When the nut 11 is rotated in this embodiment, friction arises between the movable magnetic member 36 and fixed magnet 37s under the influence of the weight of the movable magnetic member 36. This friction can be reduced by, for instance, suspending the movable magnetic member 36 from the nut 11 using a spring whose force substantially correspond to the weight of the movable magnetic member 36. By this means, the weight of the movable magnetic member 36 becomes apparently zero and, therefore, said friction also is reduced to zero or very little. Consequently, occurrence of abrasive wear between the movable magnetic member 36 and fixed magnet 37s can be sufficiently prevented.

In the loading shaft positioning apparatus according to this invention, as described above, the loading shaft is elevated to a given position and the detector that detects its arrival at the given position then operates to bring the electromagnetic clutch or brake, serving as electromagnetic means, into engagement with the operating nut. Consequently, the elevation of the loading shaft is automatically discontinued and said shaft is set in the given position. This remarkably simplifies the positioning procedure of the loading shaft.

What is claimed is:

1. Semi-automatic loading shaft positioning apparatus for a hardness tester, comprising;
   a frame;
   a specimen supporting screw longitudinally movably fitted to the frame to longitudinally move, in use, a loading shaft by the supported specimen in one longitudinal direction for engaging the shaft with a loading lever swingably pivoted to the frame;
   a manually rotatable nut threadedly connected with the screw for effecting the screw's and specimen's and thereby the shaft's longitudinal moving toward the shaft's engagement with the loading lever;
   a detector for detecting the shaft's arrival at a given position in said longitudinal moving before said engagement; and
   an electromagnetic unit mounted on the frame opposite the nut, having an electric circuit for energizing the unit when the detector detects said position, having a magnetic circuit which includes an armature connected with the nut to normally move therewith and, upon the energizing of the unit to stop movement thereof relative to the frame, thereby semiautomatically fixing the given position of the shaft, and having an electromagnet mounted on the frame for limited movement along the screw to effect the stopping in the given position of the shaft but to avoid applying a vertical magnetic force to the shaft when the shaft has been moved into contact with the specimen by the loading lever.

2. Apparatus according to claim 1, wherein the electromagnetic unit comprises an electromagnetic clutch.

3. Apparatus according to claim 1, wherein the electromagnetic unit comprises an electromagnetic brake.

4. Apparatus according to claim 3, wherein said electromagnetic brake comprises a movable magnetic member mounted below the operating nut to be movable therewith and an electromagnetic unit fitted to the frame for attracting and fixing the movable magnetic member when the detector detects said position of the shaft.

* * * * *